United States Patent
Kamppari et al.

[11] Patent Number: 5,758,640
[45] Date of Patent: Jun. 2, 1998

[54] ARRANGEMENT FOR FILLING AND EMPTYING AN ANAESTHETIC VAPORIZER

[75] Inventors: Lasse Kamppari; Antti Särelä, both of Espoo; Jukka Kankkunen, Vantaa, all of Finland

[73] Assignee: Instrumentarium Oy, Helsinki, Finland

[21] Appl. No.: 774,270

[22] Filed: Dec. 27, 1996

[30] Foreign Application Priority Data

Dec. 29, 1995 [FI] Finland ............. 956354
Apr. 18, 1996 [FI] Finland ............. 961698
Oct. 18, 1996 [FI] Finland ............. 964205

[51] Int. Cl.⁶ ............. A62B 9/04; A61M 15/00; A61M 16/00; B65B 1/04
[52] U.S. Cl. ............. 128/202.27; 128/203.19; 141/18
[58] Field of Search ............. 128/202.27, 203.19; 141/18, 285, 325, 326

[56] References Cited

U.S. PATENT DOCUMENTS

| | | |
|---|---|---|
| 3,565,133 | 2/1971 | Jones . |
| 3,575,168 | 4/1971 | Jones et al. . |
| 3,842,870 | 10/1974 | Burgess ............. 141/326 |
| 4,693,853 | 9/1987 | Falb et al. ............. 128/202.27 |
| 4,719,949 | 1/1988 | Mears ............. 141/325 |
| 4,747,508 | 5/1988 | Sherwood ............. 141/326 |
| 4,883,049 | 11/1989 | McDonald ............. 128/202.27 |
| 5,144,991 | 9/1992 | Wallroth et al. ............. 141/18 |
| 5,381,836 | 1/1995 | Braatz et al. . |
| 5,474,112 | 12/1995 | Carola ............. 141/18 |
| 5,478,506 | 12/1995 | Lavimodiere ............. 128/202.27 |
| 5,505,236 | 4/1996 | Grabenkort et al. . |
| 5,585,045 | 12/1996 | Heinonen et al. ............. 128/202.27 |

FOREIGN PATENT DOCUMENTS 2279016 12/1994 United Kingdom .

*Primary Examiner*—Kimberly L. Asher
*Attorney, Agent, or Firm*—Andrus, Sceales, Starke & Sawall

[57] ABSTRACT

An arrangement in connection with an anaesthetic vaporizer, said arrangement comprising a filling head to be connected to a liquid container of the anaesthetic vaporizer, said filling head being provided with a connection point for an anaesthetic supply container or the like. The filling head comprises a filling conduit adapted to form a flow connection between the connection point for an anaesthetic supply container or the like and the liquid container of the anaesthetic vaporizer for filling the liquid container with an anaesthetic, and a discharge conduit adapted to form a passage through which the anaesthetic in the liquid container of the anaesthetic vaporizer can be discharged to an anaesthetic supply container or the like. To prevent erroneous filling, the discharge conduit is adapted to form a flow connection between the liquid container and the connection point provided in the filling head for an anaesthetic supply container or the like, and the discharge conduit is provided with a separate cut-off device arranged to close the flow connection formed by the discharge conduit.

11 Claims, 2 Drawing Sheets

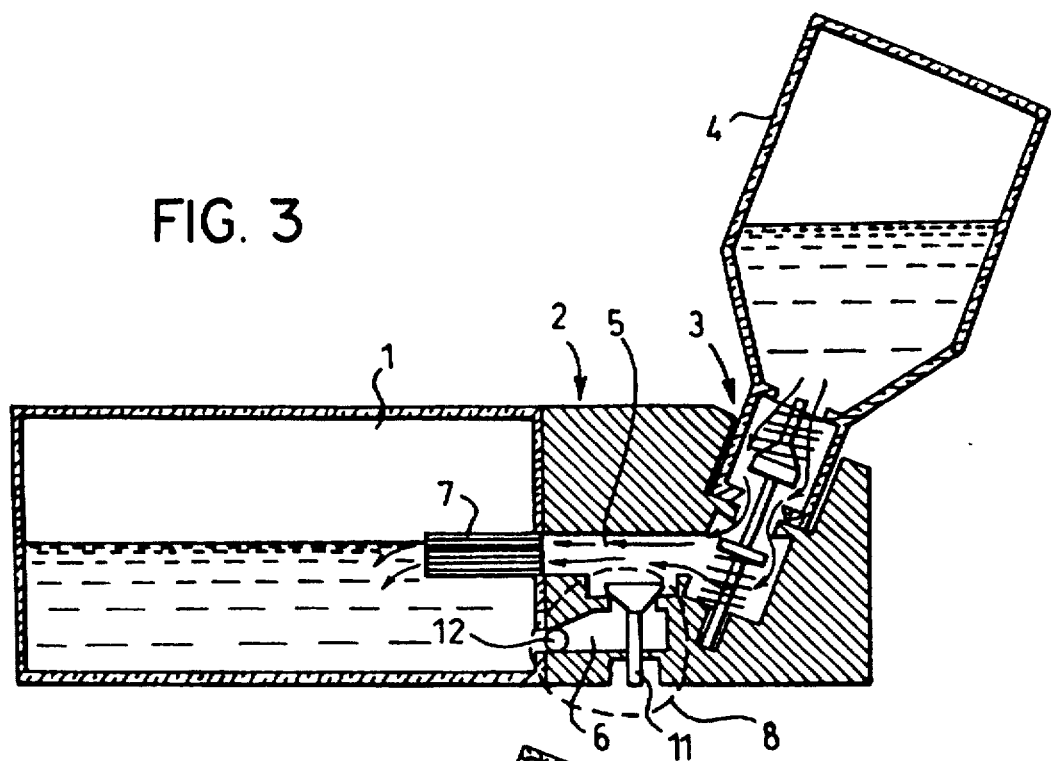
FIG. 3
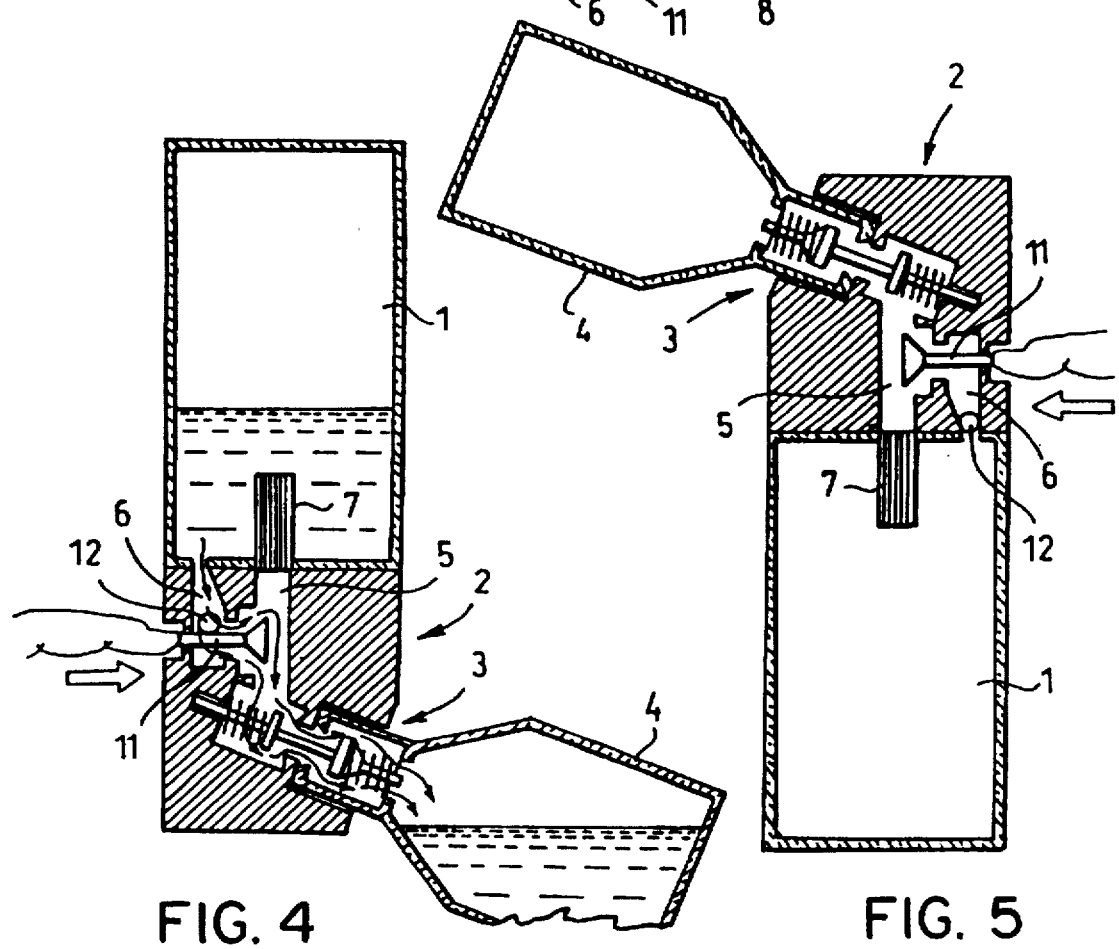
FIG. 4
FIG. 5

ARRANGEMENT FOR FILLING AND EMPTYING AN ANAESTHETIC VAPORIZER

BACKGROUND OF THE INVENTION

The invention relates (to an arrangement for use with an anaesthetic vaporizer. The arrangement comprises a filling head to be connected to a liquid container of the anaesthetic vaporizer, said filling head being provided with a connection point for an anaesthetic supply container or the like and a filling conduit adapted to form a flow connection between the connect point for an anaesthetic supply container or the like and the liquid container of the anaesthetic vaporizer for filling the liquid container with an anaesthetic. The filling head also includes discharge conduit adapted to form a passage through which the anaesthetic in the liquid container of the anaesthetic vaporizer can be discharged to an anaesthetic supply container or the like.

All anaesthetic vaporizers of the prior art comprise a liquid container from which an anaesthetic is conducted to the other elements of the vaporizer either as vapour or liquid. The liquid in the container is consumed during anaesthesia, wherefore anaesthetic must naturally be added to the container from time to time. Sometimes it is also necessary to empty the liquid container or the anaesthetic. It should also be noted that standards, e.g. CSA Z168.3, item 12.2.2.1, define that it must be possible to empty the vaporizer or the anaesthetic.

There are numerous solutions for filling and emptying the liquid container of an anaesthetic vaporizer. Solutions of two main types have been previously used in the field. One of the main types is a key-filler-type filling mechanism, which has been available for a long time. The key-filler-type filling mechanism is a rectangular keyed filling system defined by the standard proposal EN 1280. The other known main type is solutions disclosed, for example, in U.S. Pat. No. 5,505,236 and 5,381,836.

In the key-filler-type filling mechanism the anaesthetic liquid container is both filled and emptied through a separate key-filler adaptor provided between the anaesthetic bottle and the container. In the filling position, the anaesthetic bottle is located above the filling mechanism and the liquid surface of the anaesthetic container, whereby the anaesthetic liquid flows from the bottle to the container under the force of gravity. In the emptying position, the anaesthetic bottle is located below the filling mechanism and the liquid surface of the liquid container, whereby the anaesthetic liquid flows from the container to the bottle under the force of gravity. The filling head of the anaesthetic liquid container may comprise separate conduits for filling and emptying. In this case, there is a separate discharge valve for emptying. In some solutions, such as the Aladin™ liquid container of Datex-Engström, the same conduit is used for both filling and emptying, wherefore a separate discharge valve is not needed.

The solution described above has the advantage that the filling and emptying take place through the same key-filler adaptor. The problems with these types of solutions are their technical reliability and the fact that they are difficult to use. Because of these problems, filling systems that are more reliable and easier to use have been developed in the field. Filling mechanisms that are technically more advanced and easier to use are disclosed, for example, in the above-mentioned U.S. Pat. Nos. 5,505,236 and 5,381,836.

U.S. Pat. No. 5,505,236 discloses a filling mechanism according to which a container is filled through a filling head fixedly mounted on an anaesthetic bottle. During the filling, the filling head engages directly with a complementary portion provided in the filling head of the anaesthetic liquid container. Such a filling mechanism has been found to be technically better and easier to use than the key-filler-type filling mechanism described above. However, in such a solution, the container cannot be emptied through the same complementary portion and filling head. In this solution, the container is emptied through a separate emptying port, which must be opened with a tool. The filling head of the anaesthetic bottle is provided with a separate emptying adaptor, which can be connected to the emptying port provided in the container. There are, however, problems associated with these types of emptying solutions. First, a separate loose emptying adaptor is required. Second, it is possible to open the emptying port with a tool even if the emptying adaptor and the bottle are not in place, whereby the liquid drains out in an uncontrolled manner. Third, the container can be filled through the emptying conduit, bypassing the actual filling conduit and a mechanism for preventing overfill. The solution disclosed in U.S. Pat. No. 5,381,836 does not allow the container to be filled and emptied through the same complementary portion, either.

BRIEF SUMMARY OF THE INVENTION

It is an object of the invention to eliminate the drawbacks of the prior art and to combine the advantages of the known solution types. This is achieved with the arrangement of the invention, which is characterized in that the discharge conduit is adapted to form a flow connection between the liquid container and the connection point provided in the filling head for an anaesthetic supply container or the like, and that the discharge conduit is provided with a separate cut-off device arranged to close the flow connection formed by the discharge conduit.

The most significant advantage of the invention is that the anaesthetic vaporizer is filled and emptied through one and the same connection point provided for the filling container or the like, i.e. through the same complementary part. No separate parts or adaptors are needed, wherefore the container can be both filled and emptied in a simple manner. The invention also eliminates the possibility of the anaesthetic agent draining out in an uncontrolled manner as a result of misuse of the emptying mechanism. Furthermore, the invention makes it possible to provide a solution which does not allow the container to be filled bypassing the filling conduit and overfill mechanism. Yet another advantage of the invention is that it is suitable for very different solutions, particularly a vaporizer or liquid container which can be turned without breaking the device or risking the patient's health. Furthermore, the arrangement of the invention is simple in construction, wherefore the start-up and operating costs will be low.

BRIEF DESCRIPTION OF THE SEVERAL VIEWS OF THE DRAWINGS

In the following, the invention will be described in greater detail by means of the preferred embodiments illustrated in the accompanying drawings, in which FIGS. 3 to 5 illustrate schematically the operation of the arrangement of the invention in different situations.

DETAILED DESCRIPTION OF THE INVENTION

Figure 1:
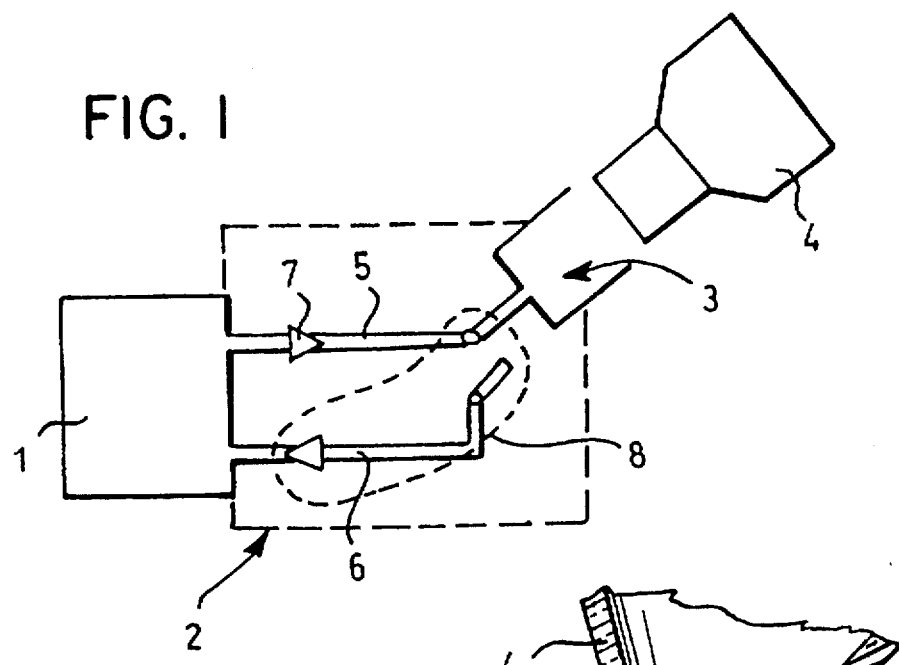
FIG. 1 is a schematic view of an arrangement of the invention.

FIG. 1 is a schematic view of the operation and structure of the arrangement of the invention. Reference numeral 1 indicates a liquid container of an anaesthetic vaporizer. Reference numeral 2 designates a filling head to be connected to the anaesthetic vaporizer. The filling head is provided with a connection point 3 for an anaesthetic supply container or the like 4. Reference numeral 5 indicates a filling conduit which forms a flow connection between the connection point 3 for the anaesthetic supply container or the like 4 and the liquid container 1 of the anaesthetic vaporizer. Reference numeral 6 designates a discharge conduit, through which the anaesthetic in the liquid container 1 of the anaesthetic vaporizer can be discharged to the anaesthetic supply container or the like. The term 'anaesthetic supply container or the like' refers in this example to an anaesthetic bottle, i.e. a container serving as an anaesthetic transport or supply container, or some other container adapted to engage with the connection point 3. Reference numeral 7 denotes a mechanism for preventing overfill.

According to the essential idea of the invention, the discharge conduit 6 forms a flow connection between the liquid container 1 and the connection point 3 provided in the filling head for the anaesthetic supply container of the like 4. The discharge conduit 6 is provided with a separate cut-off device 8, which closes the flow connection formed by the discharge conduit 6. The separate cut-off device 8 is indicated in FIG. 1 by a broken line. The separate cut-off device 8 can be formed in different ways, as will be explained below.

Figure 2:
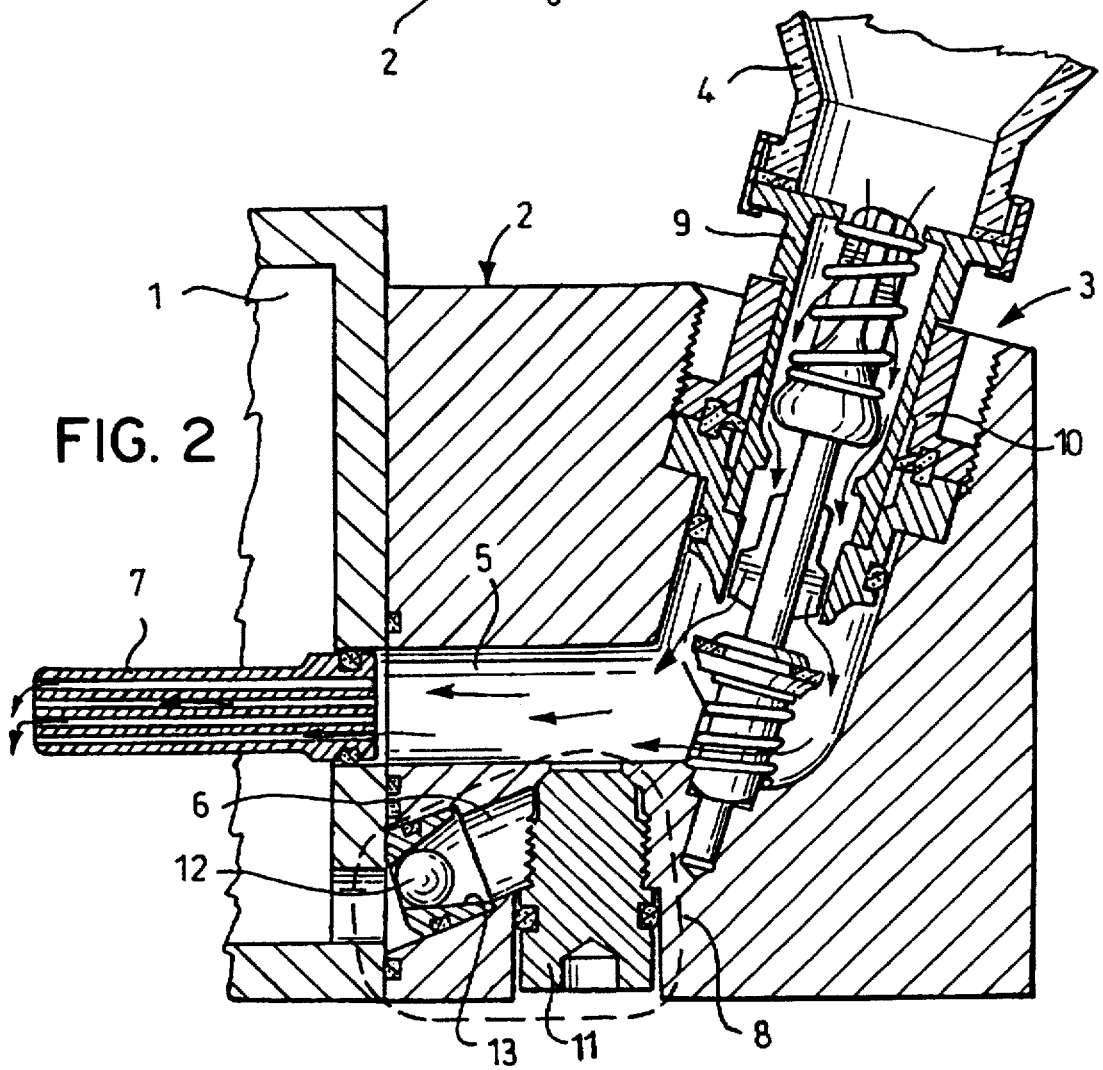
FIG. 2 is a cross-sectional side view of a first embodiment of the invention.

FIG. 2 illustrates a first, or the most preferred, embodiment of the arrangement of the invention. In FIG. 2, the same numbers have the same significance as in FIG. 1. As can be seen from FIG. 2, the anaesthetic supply container or the like 4 is provided with a valve mechanism 9 which engages with the complementary part 10 in the filling head. When the supply container or the like 4 is inserted in the connection point 3 in the filling head, the anaesthetic flows through the filling conduit 5 and the overfill prevention mechanism 7 to the liquid container 1 of the anaesthetic vaporizer, as indicated by arrows in FIG. 2.

To allow the container to be emptied, the filling head is provided with a discharge conduit 6, which forms a flow connection between the liquid container 1 and the connection point 3, as stated above. The discharge conduit 6 is provided with a separate cutoff of device 8 for closing the discharge conduit 6 when it is not in use. The cut-off device 8 comprises a mechanical element, which may be a cut-off valve 11 (e.g. a screw valve) or a cut-off member 12 (e.g. a ball). The cut-off member 12 is arranged to move against the sealing surface 13 to close the discharge conduit 6 whenever the filling head 2 is not in the liquid container emptying position (i.e. the ball closes the discharge conduit whenever the filling head is in some other position than the emptying position), and correspondingly to move away from the position closing the discharge conduit 6 when the filling head 2 is in the emptying position. The cut-off device may also be a combination of a cut-off valve 11 and a cut-off member, as in the example of FIG. 2. The cut-off member 12 can be arranged to move to a position closing the discharge conduit under the force of gravity, for example, such that the discharge conduit is open only when the filling head 2 is in the emptying position. The filling head 2 can be fixedly mounted on the container 1, whereby the filling head is placed in the emptying position by turning the container 1 to this position. If the container is heavy or otherwise unsuitable for changing position, the filling head 2 can be mounted displaceably on the container 1: the filling head 2 can thus be displaced (e.g. turned from the filling position to the emptying position or vice versa) in such a manner that the actual container remains stationary. However, it is naturally possible to connect the filling head to the container in such a way that the filling head can be placed in the emptying position irrespective of the position of the container. In the example of FIG. 2, the valve 11 is a screw valve to be moved with a suitable tool, e.g. a hexagonal wrench. The cut-off valve may also be a valve other than the screw valve shown in FIG. 2. An example of other suitable valves is a disc valve. When the cut-off valve is a disc valve, it can naturally be mounted according to the invention such that the pressure of the liquid container closes the valve (pressure to close), or such that the pressure of the liquid container opens the valve (pressure to open) The cut-off valve may also be a ball valve, seat valve or some other valve with the same function.

In the following, the operation of the arrangement of the invention will be described in greater detail by means of the example shown in FIGS. 3 to 5. in FIGS. 3 to 5, the same numbers have the same significance as in FIGS. 1 and 2. FIG. 3 shows the arrangement of the invention during filling, i.e. in the same situation as in FIG. 2. FIG. 4, in turn, illustrates the emptying process, i.e. a situation where the container is emptied through a discharge conduit to an anaesthetic supply container or the like. FIG. 5 illustrates a situation where someone is trying to fill the container erroneously through the discharge conduit.

FIG. 3 illustrates the operation of the arrangement of the invention during filling. In the arrangement of the invention, the liquid container 1 can be filled, for example, using the valve mechanism principle disclosed in the above-mentioned U.S. Pat. No. 5,505,236. It would also be possible to use the principle disclosed in U.S. Pat. No. 5,381,836. When the container is filled, the anaesthetic flows from the supply container of the like to the connection point 3. The connection point 3 is formed by means of various sealings, valves and other structures known per se. From the connection point 3, the anaesthetic flows through the filling conduit 5 and the overflow prevention mechanism 7 to the container 1. In the example of FIG. 2, the overflow prevention mechanism 7 is an intermediate container formed from a curved tubular portion, e.g. a U-shaped tubular portion, disclosed e.g. in Finnish patent applications Ser. Nos. 956354 and 961698 (see corresponding U.S. patent application Ser. No. 08/769,957 filed Dec. 19, 1996). The tubular portion may curve in a stepwise or stepless manner. It will be obvious, however, that even other kinds of overflow prevention mechanisms can be used with the invention. In the situation illustrated in FIG. 3, the separate cut-off device 8 of the discharge conduit 6 is in a position closing the discharge conduit. In the example of FIG. 3, the separate cutoff device 8 consists of a disc valve 11 and a ball 12 moving under the force or gravity.

FIG. 4 illustrates the operation of the arrangement of the invention during emptying. In the emptying process, the discharge conduit, which is separate from the filling conduit, is connected to the filling conduit. The connection is effected in the example of FIG. 4 by turning the container 1- and thereby also the filling head 2- to the emptying position and opening the cut-off valve 11. The ball 12 moves by gravity from the sealing surface to a position in which the discharge conduit 6 is open, whereby the anaesthetic is allowed to flow to the filling conduit and further to the supply container or the like 4, as indicated by the arrows in FIG. 4. The embodiment shown in FIG. 4 comprises both a cut-off valve 11 operated by a user and a cut-off member, or ball 12, operating by gravity. It will be obvious that the invention can also be implemented by means of either a cut-off valve operated by a user or a member moving under the force of gravity. Instead of a disc valve, it is also possible to use some other valve construction, e.g. a screw valve as in FIG. 2.

FIG. 5 illustrates the arrangement of the invention during misuse, i.e. in a situation where someone is trying to fill the container 1 through the discharge conduit 6. When the filling head is in a position where the liquid surface off the supply container or the like 4 is above the liquid surface of the liquid container 1, as shown in FIG. 4, the discharge conduit 6 does not open, and the filling does not succeed. The cut-off valve 11 can be opened in the position of FIG. 5, but the ball 12 closes the discharge conduit 6 under the force of gravity, whereby it is impossible to fill the container through the conduit. This is illustrated in FIG. 5. The container can be emptied only when the filling head moves to the emptying position, whereby the cut-off member (e.g. a ball) closing the discharge conduit rolls away from the sealing surface and thereby opens the discharge conduit. In this situation, the liquid surface of the liquid container 1 is above the liquid surface of the anaesthetic supply container or the like, wherefore overfill is prevented.

The embodiments described above are not intended to limit the invention in any way, but the invention can be modified fully freely within the scope of the appended claims. It will thus be clear that the arrangement of the invention or its details need not be precisely as shown in the figures, but other solutions are also possible.

We claim:

1. An arrangement for filling and emptying a liquid container of an anaesthetic vaporizer from an anaesthetic supply container, said arrangement comprising:

filling head connectable to the liquid container of the anaesthetic vaporizer, said filling head being provided with a connection point for the anaesthetic supply container and a filling conduit adapted to form a flow connection between the connection point for the anaesthetic supply container and the liquid container of the anaesthetic vaporizer for filling the liquid container with an anaesthetic, and a discharge conduit adapted to form a flow connection passage between the liquid container and the connection point for the anaesthetic supply container through which the anaesthetic in the liquid container of the anaesthetic vaporizer can be discharged to the anaesthetic supply container, and a separate cut-off device provided in the discharge conduit and arranged to close the flow connection passage formed by the discharge conduit.

2. An arrangement according to claim 1, wherein the cut-off device comprises a mechanically operable member.

3. An arrangement according to claim 2, wherein the mechanically operable member comprises a cut-off valve.

4. An arrangement according to claim 3, wherein the cut-off valve is a screw valve.

5. An arrangement according to claim 2, wherein the filling head has a liquid container emptying position in which the anaesthetic can flow through the discharge conduit from the liquid container to the anaesthetic supply container, and wherein the mechanically operable member comprises a cut-off member mounted in the discharge conduit and arranged to move under the force of gravity against a sealing surface to close the discharge conduit when the filling head is in a position other than the liquid container emptying position and, correspondingly, to move away from the position closing the discharge conduit when the filling head is in the emptying position.

6. An arrangement according to claim 5 further including a cut-off valve provided in said discharge conduit.

7. An arrangement according to claim 6, wherein the filling head is arranged to be displaceably connectable to the liquid container of the anaesthetic vaporizer such that it can be displaced from a filling position to the emptying position and vice versa.

8. An arrangement according to claim 7, wherein the filling head is arranged to be displaced from the filling position to the emptying position irrespective of the position of the liquid container.

9. An arrangement according to claim 5, wherein the filling head is arranged to be displaceably connectable to the liquid container of the anaesthetic vaporizer such that it can be displaced from a filling position to the emptying position and vice versa.

10. An arrangement according to claim 9, wherein the filling head is arranged to be displaced from the filling position to the emptying position irrespective of the position of the liquid container.

11. An arrangement according to claim 1, wherein the filling conduit is arranged to open to the liquid container through an overfill prevention mechanism provided by means of an intermediate container formed from a curved tubular member.

* * * * *